United States Patent [19]

Rubenstein

[11] Patent Number: 5,891,858

[45] Date of Patent: Apr. 6, 1999

[54] ANTISENSE POLYNUCLEOTIDE INHIBITION OF HUMAN GROWTH FACTOR-SENSITIVE CANCER CELLS

[75] Inventor: Marvin Rubenstein, Skokie, Ill.

[73] Assignee: Hektoen Institute for Medical Research, Chicago, Ill.

[21] Appl. No.: 733,204

[22] Filed: Oct. 17, 1996

Related U.S. Application Data

[62] Division of Ser. No. 200,924, Feb. 22, 1994, Pat. No. 5,610,288, which is a continuation of Ser. No. 9,596, Jan. 27, 1993, abandoned.

[51] Int. Cl.⁶ .................................................. A01N 43/04
[52] U.S. Cl. ................ 514/44; 435/6; 435/69.1; 436/501; 536/23.1; 536/24.1; 536/24.3; 536/24.31; 536/24.32; 536/24.33; 935/77; 935/78
[58] Field of Search ................... 435/6, 69.1, 7.1, 435/7.2, 810; 436/501; 536/23.1, 24.1, 24.3–33; 935/77,78; 514/44

[56] References Cited

U.S. PATENT DOCUMENTS

| | | | |
|---|---|---|---|
| 4,740,463 | 4/1988 | Weinberg et al. | 435/172.3 |
| 4,816,561 | 3/1989 | Todaro | 530/324 |
| 4,863,899 | 9/1989 | Todaro | 514/9 |
| 4,999,421 | 3/1991 | Brunck et al. | 530/350 |
| 5,004,810 | 4/1991 | Draper | 536/27 |
| 5,087,617 | 2/1992 | Smith | 514/44 |
| 5,098,890 | 3/1992 | Gewirtz et al. | 514/44 |
| 5,107,065 | 4/1992 | Shewmaker et al. | 800/205 |
| 5,132,408 | 7/1992 | Baird et al. | 530/399 |
| 5,135,917 | 8/1992 | Burch | 514/44 |

FOREIGN PATENT DOCUMENTS

WO 91/01141  2/1991  WIPO .

OTHER PUBLICATIONS

Sizeland et al. (1992), Molecular Biology of the Cell, vol. 3, No. 11, pp. 1235–1243.
Stein et al. (1993) Science, vol. 261, pp. 1004–1012.
New England Biolabs 1986/87 Catalog, pp. 60–62.
Rubenstein et al., Poster No. 31, 1992 *International Symposium on Biology of Prostate Growth*, National Institute of Diabetes, and Digestive and Kidney Diseases, (Sep. 11–13, 1992), Bethesda, MD.
Rubenstein et al., *Society For Basic Urologic Research*, 1992 Annual Fall Symposium (Oct. 3–6, 1992), St. Louis, MO.
*Stedman's Medical Dictionary*, 22nd ed., The Williams and Wilkins Co., Baltimore (1972) pp. 204, 205, 421, 468, and 1119.
*Journal of Cellular Biology*, Supplement 17E, 1993, Abstracts S022 (p. 191) and S027 (p. 192) and Arnold et al. (no page number), 1993.
Wilding, *The Prostate,15*:1–12 (1989).
Rubenstein et al., *Clin. Physiol. Biochem.*, 9:47–50 (1992).
Aaronson et al., *In: Molecular Foundations of Oncology*, S. Broder (ed.), Williams and Wilkins, Baltimore, MD., pp. 27–39, (1991).
Todd et al, *J. Dent. Res.*, 70:917–923 (1991).
Marshall et al., *Science*, 259: 1564–1570 (1993).
Gutierrez et al., *The Lancet*, 359:715–721 (1992).
Naraganan et al., *Oncogene*, 7:553–561 (1992).
Ullrich et al., *Nature*, 307:418–425 (1984).
Tseng et al, *Cancer Gene Therapy*, 1:65–71 (1994).
Vander Krol et al, *Biotechniques*, 6:958–976 (1988).
Hunts et al, *FEBS Let.*, 206,319–322 (1986).
Baserga et al, *Ann. NY Acad. Sci*, 600:64–69 (1992).
Neckers et al, *Ann. NY Acad. Sci*, 600:37–44 (1992).

*Primary Examiner*—Ardin H. Marschel
*Attorney, Agent, or Firm*—Welsh & Katz, Ltd.

[57] ABSTRACT

Antisense polynucleotides to human transforming growth factor alpha (TGF-α) and the receptor for human epidermal growth factor (rEGF) are disclosed. Those polynucleotides are about 30 to about 50 bases in length and each hybridizes to about 10 to about 25 bases flanking the start codon for the gene encoding those proteins. Use of those antisense polynucleotides alone, together and mixed with an antibody combining site-containing molecule that binds to rEGF in treating human growth factor-sensitive cancerous tumors such as prostate tumors is also disclosed.

2 Claims, No Drawings

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

CTGTCCAGCC GAGGGGACCA TTTTACGGGC GGGCGGGCA     3 9

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..3
        ( D ) OTHER INFORMATION: /function= "N represents bases modified by a phosphorothioate bond."

( i x ) FEATURE:
    ( A ) NAME/KEY: misc_feature
    ( B ) LOCATION: 37..39
    ( D ) OTHER INFORMATION: /function= "N represents bases modified by a phosphorothioate bond."

( x i ) SEQUENCE DESCRIPTION: SEQ ID NO:2:

NNNTCCAGCC GAGGGGACCA TTTACGGGC GGGCGGNNN    39

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

GGCCGTCCCG GAGGGTCGCA TCGCTGCTCC CCGAAGAGC    39

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..3
        ( D ) OTHER INFORMATION: /function= "N represents bases modified by a phosphorothioate bond."

( i x ) FEATURE:
        ( A ) NAME/KEY: misc_feature
        ( B ) LOCATION: 37..39
        ( D ) OTHER INFORMATION: /function= "N represents bases modified by a phosphorothioate bond."

( x i ) SEQUENCE DESCRIPTION: SEQ ID NO:4:

NNNCGTCCCG GAGGGTCGCA TCGCTGCTCC CCGAAGNNN    39

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

CTGTCCAGCC GAGGGGACCA TTTACGGGC GGGCGGGCAG    40

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

CTGTCCAGCC GAGGGGACCA TTTTACGGGC GGGCGGGCAG C          41

( 2 ) INFORMATION FOR SEQ ID NO:7:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

GGGCGAGCTG TCCAGCCGAG GGACCATTT TACGGGCGGG CGGGCAGCAG GCT          53

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

ACGGGCGGGC GGGCATTTTA CCAGGGGAGC CGACCTGTC          39

( 2 ) INFORMATION FOR SEQ ID NO:9:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

TCGGACGACG GGCGGGCGGG CATTTTACCA GGGGAGCCGA CCTGTCGAGC GGG          53

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..3
        ( D ) OTHER INFORMATION: /function= "N represents bases
        modified by phosphorothioate bonds."

( i x ) FEATURE:
        ( A ) NAME/KEY: misc_feature
        ( B ) LOCATION: 37..39
        ( D ) OTHER INFORMATION: /function= "N represents bases
        modified by phosphorothioate bonds."

( x i ) SEQUENCE DESCRIPTION: SEQ ID NO:10:

NNNGGCGGGC GGGCATTTTA CCAGGGGAGC CGACCTNNN          39

( 2 ) INFORMATION FOR SEQ ID NO:11:

( i ) SEQUENCE CHARACTERISTICS:

( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

CTGCCCCGGC CGTCCCGGAG GGTCGCATCG CTGCTCCCCG AAGAGCTCGC TCC    53

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

CGAGAAGCCC CTCGTCGCTA CGCTGGGAGG CCCTGCCGG    39

( 2 ) INFORMATION FOR SEQ ID NO:13:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

CCTCGCTCGA GAAGCCCTC GTCGCTACGC TGGGAGGCCC TGCCGGCCCC GTC    53

( 2 ) INFORMATION FOR SEQ ID NO:14:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..3
        ( D ) OTHER INFORMATION: /function= "N represents bases
            modified by phosphorothioate bonds."

( i x ) FEATURE:
        ( A ) NAME/KEY: misc_feature
        ( B ) LOCATION: 37..39
        ( D ) OTHER INFORMATION: /function= "N represents bases
            modified by phosphorothioate bonds."

( x i ) SEQUENCE DESCRIPTION: SEQ ID NO:14:

NNNGAAGCCC CTCGTCGCTA CGCTGGGAGG CCCTGCNNN    39

ANTISENSE POLYNUCLEOTIDE INHIBITION OF HUMAN GROWTH FACTOR-SENSITIVE CANCER CELLS

This is a division of application Ser. No. 08/200,924, filed Feb. 22, 1994, now U.S. Pat. No. 5,610,288; which is a continuation of application Ser. No. 08/009,596, filed Jan. 27, 1993, now abandonded.

DESCRIPTION

TECHNICAL FIELD

The present invention relates to growth-factor related polynucleotides and their use in inhibiting the growth of prostate cancer, and more specifically to antisense molecules corresponding in sequence to portions of the mRNA encoding human transforming growth factor alpha (TGF-α) and the receptor for human epidermal growth factor (rEGF), and their use in inhibiting the growth of human growth factor-sensitive cancer cells such as prostate cancer cells.

BACKGROUND OF THE INVENTION

Antisense polynucleotides contain synthetic sequences of nucleotide bases complementary to messenger RNA (mRNA or message) or the sense strand of double stranded DNA. Admixture of sense and antisense polynucleotides under appropriate conditions leads to the binding of the two molecules, or hybridization.

When these polynucleotides bind to (hybridize with) mRNA, inhibition of protein synthesis (translation) occurs. When these polynucleotides bind to double stranded DNA, inhibition of RNA synthesis (transcription) occurs. The resulting inhibition of translation and/or transcription leads to an inhibition of the synthesis of the protein encoded by the sense strand such as protein of the tissues, and more importantly here, a cellular growth factor, growth factor receptor, oncogene or protooncogene (many of which act as growth factors, receptors or mediators of signal transduction).

Previous reports have described antisense RNA inhibition of growth hormone production in rat pituitary tumor cells [Paulssen et al., *Biochem. Biophys. Res. Commun.*, 171:293–300 (1990)], cytoplasmic Raf-1 protein kinase in NIH/3T3 cells [Kolch et al., *Nature*, 349:426–428 (1991), and E-cadherin in highly invasive epithelial tumors of dog or mouse mammary gland origin [Vleminckx et al., *Cell*, 66:107–119 (1991)].

In one study, an antisense RNA complementary to the protooncogene c-myc sequence of the HL-60 promyelocytic leukemia cell line reduced c-myc expression, leading to cellular differentiation. The expression of c-myc was inhibited at both translational and transcriptional levels. The RNA—RNA duplex formed increased the levels of two proteins (74 and 110 Kd). The 74 Kd protein, acting as a negative repressor, binds to the CACCTCC repeat found in the c-myc leader sequence and inhibits c-myc mRNA transcription resulting in monocytic differentiation. Yokoyama, In: Prospects for Antisense Nucleic Acid Therapy of Cancer and AIDS, E. Wickstrom (ed), Wiley-Liss, New York, 1991, pp. 35–51.

Reports on antisense DNA have included inhibition of growth hormone production in lymphocytes [Weigent et al., *Endocrinology*, 128:2053–2057 (1991)], reduction of EGF receptors in human cells [Yamada et al., *Exp. Cell Res.*, 184:90–98 (1989)], reduction of N-myc expression [Schilbach et al., *Biochem. Biophys. Res. Commun.*, 170:1242–1248 (1990); Whitesell et al., *Mol. Cell. Biol.*, 11:1360–1371 (1991); Rosolen et al., *Cancer Res.*, 50:6316–6322 (1990)], inhibition of c-myc expression in human breast cancer [Watson et al., *Cancer Res.*, 51:3996–4000 (1991)] and lymphoma [McManaway et al., *Lancet*, 335:806–811 (1990)], inhibition of K-ras in lung cancer [Mukhopadhyay et al., *Cancer Res.*, 51:1744–1748 (1991)], c-myb in colon cancer [Melani et al., *Cancer Res.*, 51:2897–2901 (1991)], and ras p21 expression [Chang et al., *Biochemistry*, 30:8283–8286 (1991)]. In the most successful instances, antisense sequences, utilizing either RNA or DNA polynucleotides, can direct partial or complete reversion of malignant phenotypes. Ledwith et al., *Mol. Cell Biol.*, 10:1545–1555 (1990); Sklar et al., *Mol. Cell. Biol.*, 11:3699–3710 (1991).

Of particular interest in treating human malignancies is the inhibition by antisense polynucleotides of expression of the BCR-ABL gene in chronic myelogenous leukemia. Szczylik et al., *Science*, 253:562–565 (1991). In this case a functional BCR-ABL gene maintained the leukemic phenotype and treatment with antisense DNA, directed towards the BCR-ABL junction, suppressed leukemic colony formation.

Whereas many antisense probes are directed to the translation initiation (AUG) site, other antisense probes have been directed towards intron excision sites of pre-mRNA. Volloch et al., *Biochem. Biophys. Res. Commun.*, 179:1593–1599 (1991); Munroe, *EMBO J.*, 7:2523–2532 (1988); Munroe et al., *J. Biol. Chem.*, 266:22063–22068 (1991). In some cases, where the excision is incorrect, such an approach permits the selective targeting of malignant cells that express unique DNA sequences, while sparing their normal counterparts. Such tumor cell selectivity is not possible with conventional chemo- or radiation therapy.

Burkitt lymphoma is associated with abnormal expression of the c-myc oncogene due to a DNA translocation which joins the c-myc oncogene on chromosome 8 to either of the immunoglobulin genes encoded on chromosomes 2, 14 or 22. In some cases, as a result of an abnormal excision of intron mRNA, nascent transcripts may persist in a transformed clone. Antisense DNA synthesized complementary to these abnormal intron sequences greatly inhibited the ST486 and JD38 cell lines [Rosolen et al., *Cancer Res.*, 50:6316–6322 (1990)] and therefore selectively targeted only the cells with abnormal intron excision.

Antisense polynucleotides can also be used to identify and quantitate the number of genes and their location in particular cells. A study in human tissue utilized in situ hybridization, in both human oral cancer and normal oral epithelium, to identify the source and targeting of transforming growth factor α (TGF-α) to proliferating cells. This study utilized $^{35}$S-labeled sense and antisense riboprobes to human TGF-α and the receptor for epidermal growth facto (rEGF) mRNA. The results suggested that the eosinophils (containing TGF-α mRNA) produce and apparently deliver TGF-α to tumor sites, where mRNA for rEGF is expressed to a greater degree by dysplastic and carcinomatous epithelium (particularly in moderately to poor differentiated types). Todd et al., *J. Dent. Res.*, 70:917–923 (1991).

Human prostate cancer tumors are often found to contain two types of cancerous cells. A first type is sensitive to (proliferates in the presence of) androgens such as the hormone testosterone. An exemplary cell line representing this human hormone-sensitive type of prostate cancer cell is the LNCap metastatic prostate adenocarcinoma cell line (ATCC CRL 1740). The second type of cancerous cells are insensitive to testosterone and are sensitive to (proliferate in the presence of) factors that these cells themselves secrete; i.e., autocrine growth factors. An exemplary cell line representing the autocrine type of human prostate cancers is the PC-3 prostate adenocarcinoma cell line (ATCC CRL 1435), or the DU 145 prostate carcinoma cell line (ATCC HTB 81).

The hormone-sensitive prostate cancer cells cause tumors that are typically slow-growing, better differentiated and are not particularly metastatic. That type of cancerous cell growth can often be arrested by androgen deprivation, such as by castration. Chemotherapeutic treatment of patients with drugs such as Lupron (leuprolide acetate) also arrests hormone-sensitive tumor growth after an initial flare (increased symptomology) in tumor growth by a mechanism that amounts to a chemically-induced castration.

Hormone-insensitive and presumably autocrine-dependent human prostate cancer cells are more aggressive and metastatic, and their metastases are usually responsible for deaths due to prostate cancers. Drugs such as Lupron are not effective in arresting growth of hormone-insensitive prostate cancer cells.

The PC-3 cell line, an established line of human prostate cancer cells, is considered an acceptable in vitro model system for studying this disease. Kaighn et al., *Invest. Urol.*, 17:16–23 (1979). This undifferentiated cell line is hormone-insensitive and was established in 1979 from a bone marrow metastasis. PC-3 cells also secrete and respond to autocrine growth factors, including transforming growth factor-alpha (TGF-α). Hofer et al., *Cancer Res.*, 51:2780–2785 (1991). TGF-α appears to stimulate PC-3 tumor cell growth by a complicated and poorly understood mechanism of signal transduction, that begins with the binding of TGF-α to the epidermal growth factor receptor (rEGF).

TGF-α is structurally and functionally related to epidermal growth factor (EGF) [Thompson, *Cancer Cells*, 2:345–354 (1990)], both of which are bound equally to rEGF because of the 35–40 percent amino acid sequence homology between the two growth factors [Marquardt et al., *Proc. Natl. Sci. USA*, 80:4684–4688 (1983)]. The in vivo precursor of TGF-α is a 160 amino acid residue membrane-bound protein (pro-TGF-α) that is cleaved to yield a soluble compound. Massague, *J. Biol. Chem.*, 265:21393–21396 (1990). This cleavage removes an extracellular portion comprised of 50 amino acids with a molecular weight of 6 Kd and is considered to be an important regulatory event [Pandiella et al., *Proc. Natl. Acad. Sci. USA*, 88:1726–1730 (1990)] that can be stimulated by phorbol esters acting via protein kinase C [Pandiella et al., *J. Biol. Chem.*, 266:5769–5773 (1991)].

The soluble TGF-α thus formed resembles EGF structurally because it has 6 characteristic cysteine residues that form 3 disulfide bonds spaced over a region of 35–40 amino acids. Davis, *New Biol.*, 2:410–419 (1990). Both TGF-α and EGF regulate the growth (as a mitogen) and differentiation of normal and malignant human prostatic tissues. Cultured human prostatic tumor lines contain elevated levels of TGF-α mRNA and proliferate in response to TGF-α. Wilding et al., *The Prostate*, 15:1–12 (1989). TGF-α appears to have both autocrine and paracrine function, stimulating physiologic activities such as cell division and angiogenesis.

When induced in transgenic mice, TGF-α has produced epithelial hyperplasia and focal dysplastic changes that resembled carcinoma in situ. Sandgren et al., *Cell*, 61:1121–1135 (1990). It is suggested that TGF-α and EGF interactions are partly responsible for the autonomous growth of PC-3 cells. Such interactions could also account for the escape from hormone dependence in advanced human prostatic cancers. Hofer et al., *Cancer Res.*, 51:2780–2785 (1991).

Regulation of signal transduction, mediated through ligand binding to the rEGF, has been attempted both experimentally and clinically. The monoclonal antibody MAb 425 (available from Hybritech, Inc., San Diego, Calif.), which is directed against the rEGF, blocks EGF dependent functions such as mitogenesis and phosphorylation. MAb 425 has also been shown to block the TGF-α induced secondary messengers inositol-1,4,5-triphosphate and $Ca^{2+}$. Murthy et al., *Biochem. Biophys. Res. Commun.*, 172:471–476 (1990).

The sensitivity of PC-3 cells to TGF-α acting at the rEGF is further demonstrated by the lack of PC-3 cell growth in serum free media in the presence of monoclonal antibodies directed to these regulatory proteins. Hofer et al., *Cancer Res.*, 51:2780–2785 (1991). Clinically, the inhibition of prostatic tumor cell growth by suramin is thought to be mediated by blockage of TGF-α binding to the rEGF. Kim et al., *J. Urol.*, 146:171–176 (1991). TGF-α expression may also be stimulated by the ras-encoded p21 oncoprotein. Aaronson et al., In: Molecular Foundations of Oncology, S. Broder (ed.), Williams and Wilkins, Baltimore, Md., pp. 27–39, 1991.

Epidermal growth factor (EGF) is a 53-residue polypeptide, and is a potent in vitro mitogen for a variety of cell types. Harris, *Am. J. Kidney Dis.*, 17:627–630 (1991). Although the relationship of EGF to hormone (testosterone) and cellular organization (cytokeratins) is complex, EGF is implicated in the progression of prostate cancer. Fowler et al., *J. Urol.*, 139:857–861 (1988). In addition, progression of prostate cancer from hormone dependence to independence following castration is associated with a coordinate loss of growth regulatory factors. Rubenstein et al., *Clin. Physiol. Biochem.*, 9:47–50 (1992). It has been suggested that control of EGF following hormone independence might be therapeutically efficacious. Fowler et al., *J. Urol.*, 139:857–861 (1988).

Both TGF-α and EGF are degraded by metalloproteases, but involve separate degradative pathways. This level of regulation could account for some differential effects encountered in various systems. Gehm et al., *Endocrinology*, 128:1603–1610 (1991).

The human rEGF is a membrane-bound glycoprotein of 170 kd that has been identified in human prostatic tissue and the PC-3 cell line. Hofer et al., *Cancer Res.*, 51:2780–2785 (1991). The regulatory importance of rEGF is evidenced by the fact that the expression of mRNA for rEGF is greater in carcinomas of the prostate than that found in samples of benign prostatic hyperplasia, the greatest levels of rEGF mRNA being found in the human prostatic cell lines PC-3 and DU145. Morris et al., *J. Urol.*, 143:1272–1275 (1990).

Following rEGF binding of either TGF-α or EGF, tyrosine kinase activity is stimulated via signal transduction mechanisms, initiating mitogenesis. Thompson et al., *Cancer Surveys*, 4:767–788 (1985). The number of rEGF molecules found upon the cell surface correlates to cell growth regulation. In the malignant human glioma D-298 MG [Humphrey et al., *Biochem. Biophys. Res. Commun.*, 178:1413–1420 (1991)], it has been suggested that overexpression of the rEGF leads to enhanced binding by EGF and TGF-α, resulting in increased tyrosine kinase activity. Therefore overexpression, rather than a structural alteration, may account for most increases in biologic activity. Humphrey et al., *Biochem. Biophys. Res. Commun.*, 178:1413–1420 (1991).

This receptor is itself very important in growth regulation not only because it binds the EGF ligand (as well as TGF-α)

but also because the gene for this receptor is homologus to the erb-B2 and erb-B3 protooncogenes, which, when similarly overexpressed (in adenocarcinomas of the breast, stomach, ovary, colon and salivary gland) or structurally altered (in intestinal adenocarcinoma) from its protooncogene state, stimulates uncontrolled growth [Aaronson et al., In: *Molecular Foundations of Oncology*, S. Broder (ed.), Williams and Wilkins, Baltimore, Md., pp. 27–39 (1991)], probably by excessive stimulation of tyrosine kinase activity.

It would therefore be beneficial if a chemotherapeutic treatment could be devised that could arrest the growth and kill autocrine-sensitive or dependent prostate cancer cells such as those of the PC-3 cell line that are no longer susceptible to androgen deprivation therapy. The invention discussed hereinafter describes such a chemotherapeutic treatment and treating agents.

BRIEF SUMMARY OF THE INVENTION

The present invention is directed in one embodiment to a polynucleotide of about 20 to about 50, more preferably about 30 to about 40, and most preferably about 40, nucleic acid bases in length, which polynucleotide hybridizes to the about 10 to about 25; more preferably about 15 to about 20, and most preferably about 20, nucleic acid bases flanking the start codon of the mRNA encoding human transforming growth factor α. A preferred polynucleotide is an antisense molecule having the sequence shown in SEQ ID NO:1.
CTGTCCAGCCGAGGGGACCATTT-TACGGGCGGGCGGGCA (SEQ ID NO:1)

A further preferred polynucleotide links the terminal 1 to about 5 bases of SEQ ID NO:1 by pseudophosphate bonds that are resistant to cleavage by exonuclease enzymes. Preferred pseudophosphate bonds are phosphorothioate bonds.

An invert polynucleotide is also contemplated. A preferred invert polynucleotide has the sequence shown in SEQ ID NO:8.
ACGGGCGGGCGGGCATTTTACCAGGG-GAGCCGACCTGTC (SEQ ID NO:8)

The present invention is further directed to a polynucleotide of about 20 to about 50, more preferably about 30 to about 40, and most preferably about 40, nucleic acid bases in length, which polynucleotide hybridizes to the about 10 to about 25, more preferably about 15 to about 20, and most preferably about 20, nucleic acid bases flanking the start codon of the mRNA that encodes the receptor for human epidermal growth factor. A preferred polynucleotide is an antisense molecule having the sequence shown in SEQ ID NO:3.
GGCCGTCCCGGAGGGTCGCATCGCT-GCTCCCCGAAGAGC (SEQ ID NO:3)

A further preferred polynucleotide links the terminal 1 to about 5 bases of SEQ ID NO:3 by pseudophosphate bonds that are resistant to cleavage by exonuclease enzymes. Preferred pseudophosphate bonds are phosphorothioate bonds.

An invert polynucleotide is also contemplated. A preferred invert polynucleotide has the sequence shown in SEQ ID NO:12.
CGAGAAGCCCCTCGTCGCTACGCTGG-GAGGCCCTGCCGG (SEQ ID NO:12)

The present invention is still further directed to a chemotherapeutic process for killing or inhibiting the growth of human cancerous growth factor-sensitive (autocrine-sensitive) cells that comprises contacting the cells to be killed or whose growth is to be inhibited in an aqueous medium suitable for growth of those cells with a chemotherapeutic amount of a before-defined polynucleotide that hybridizes to nucleic acid bases flanking the start codon of (1) the mRNA that encodes transforming growth factor α (TGF-α), (2) the mRNA that encodes the receptor for human epidermal growth factor (rEGF), or nucleic aid bases flanking the start codon of both mRNA's, including inverts of those polynucleotides. Contact with the polynucleotide is maintained in the aqueous medium under biological culture conditions for a time period sufficient for the contacted cells to be killed or their growth inhibited. In a preferred embodiment, the growth factor-sensitive cells are prostate cancer cells.

In a still further preferred embodiment, the above chemotherapeutic process includes the further step of contacting those cells with molecules containing an antibody combining site that immunoreacts with the receptor for human epidermal growth factor (rEGF).

In one preferred embodiment, the contacting is carried out in vitro. In a further preferred embodiment, the contacting is carried out in vivo in a host mammal, and the contact is effected by administration to the mammal of a pharmaceutical composition containing the polynucleotide dissolved or dispersed in a physiologically tolerable diluent. That administration can be directly into a human cancerous tumor containing autocrine-sensitive (growth factor-sensitive) cancer cells, as well as systemically.

As is clear from the foregoing, a process of the present invention can be carried out (1) with a single polynucleotide that hybridizes with the mRNA of TGF-α or rEGF, including their respective invert polynucleotides, (2) with a combination of those polynucleotides, or (3) with a polynucleotide that hybridizes with one or both of those mRNA's in combination with antibodies directed against rEGF.

DETAILED DESCRIPTION OF THE INVENTION

A. The Polynucleotides

The present invention contemplates an antisense polynucleotide that hybridizes with mRNA molecules that encode a growth factor-related molecule, and the use of one or more of those polynucleotides in treating human growth factor-sensitive cancer cells.

One embodiment of the present invention is directed to a polynucleotide of about 20 to about 50 nucleic acid bases in length, more preferably about 30 to about 40, and most preferably about 40 nucleic acid bases in length. A contemplated polynucleotide hybridizes to the about 10 to about 25, more preferably about 15 to about 20, and most preferably about 20, nucleic acid bases flanking the start codon of the mRNA that encodes human transforming growth factor-α (TFG-α) or the mRNA for the receptor for human epidermal growth factor (rEGF).

It is not known whether a contemplated antisense polynucleotide causes an observed effect by interacting with DNA, RNA or both. The sequence for the start codon is encoded by the DNA from which the mRNA is made. A polynucleotide that hybridizes to an mRNA as discussed above corresponds in sequence to the coding strand of the DNA from which the mRNA is transcribed. As such, that same polynucleotide also hybridizes to the non-coding strand of that DNA. For ease in understanding and description, hybridization is generally discussed herein in terms of mRNA molecules with the understanding that a hybridization study can be conducted using either RNA or DNA.

As used herein, "polynucleotide" refers to a covalently linked sequence of nucleotides in which the 3' position of the pentose of one nucleotide is joined by a phosphodiester group to the 5' position of the pentose of the next nucleotide. The nucleotides can be composed of deoxyribonucleotides (DNA) or ribonucleotides (RNA). The polynucleotides exemplified herein are DNA, used for illustrative purposes only.

Polynucleotide hybridization is a function of sequence identity (homology), G+C content of the sequence, buffer salt content, sequence length and duplex melt temperature ($T_m$) among other variables. See, Maniatis et al., *Molecular Cloning*, Cold Spring Harbor Laboratory, Cold Spring Harbor, N.Y. (1982), page 388.

With similar sequence lengths, the buffer salt concentration and temperature provide useful variables for assessing sequence identity (homology) by hybridization techniques. For example, where there is at least 90 percent homology, hybridization is carried out at 68° C. in a buffer salt such as 6× SCC diluted from 20× SSC [Maniatis et al., above, at page 447]. The buffer salt utilized for final Southern blot washes can be used at a low concentration, e.g., 0.1× SSC and at a relatively high temperature, e.g. 68° C., and two sequences will form a hybrid duplex (hybridize). Use of the above hybridization and washing conditions together are defined as conditions of high stringency or highly stringent conditions.

Moderately high stringency conditions can be utilized for hybridization where two sequences share at least about 80 percent homology. Here, hybridization is carried out using 6× SSC at a temperature of about 50°–55° C. A final wash salt concentration of about 1–3× SSC and at a temperature of about 60°–68° C. are used. These hybridization and washing conditions define moderately high stringency conditions.

Low stringency conditions can be utilized for hybridization where two sequences share at least 40 percent homology. Here, hybridization carried out using 6× SSC at a temperature of about 40°–50° C., and a final wash buffer salt concentration of about 6× SSC used at a temperature of about 40°–60° C. effect non-random hybridization. These hybridization and washing conditions define low stringency conditions.

Polynucleotide hybridization of greater than about 90 percent homology (identity), and more preferably about 99 percent homology, is contemplated in the present invention, as is high stringency in hybridization studies.

One preferred polynucleotide is a human TGF-α antisense molecule having the sequence shown in SEQ ID NO:1.
C T G T C C A G C C G A G G G G A C C A T T T-
TACGGGCGGGCGGGCA (SEQ ID NO:1)

The polynucleotide of SEQ ID NO:1 contains 39 nucleic acid bases. That sequence includes 18 bases complementary to the 5'-side of the start codon (AUG) and can conveniently include one up to about seven further complementary bases from the sequence of TGF-α. Owing to the antisense nature of SEQ ID NO:1, additional bases complementary to the 5' flanking region of the TGF-α start codon mRNA are added to the 3' end of SEQ ID NO:1 as shown below for SEQ ID NO's:5 and 6:
C T G T C C A G C C G A G G G G A C C A T T T-
TACGGGCGGGCGGGCAG (SEQ ID NO:5)
C T G T C C A G C C G A G G G G A C C A T T T-
TACGGGCGGGCGGGCAGC (SEQ ID NO:6)
and so on. The additions to the 3' end of SEQ ID NO:1, from one to seven additional bases, are shown below:
G
GC
GCA
GCAG
GCAGG
GCAGGC
GCAGGCT SEQ ID NO:1 also contains 18 bases complementary to the 3' side of the mRNA start codon. A contemplated sequence can therefore include one up to about seven additional complementary bases of a TGF-α sequence linked to the 5' terminus of SEQ ID NO:1, as shown above, again because of the antisense nature of SEQ ID NO:1. The additions to the 5' end, from one to seven additional bases, are shown below:
G
AG
GAG
CGAG
GCGAG
GGCGAG
GGGCGAG In keeping with a preferred minimal length of about 30 nucleic acid bases of an antisense polynucleotide whose sequence flanks that start codon, and therefore includes the sequence hybridizing to the start codon near its center, three of the 5-'terminal and 3' terminal bases of the polynucleotide of SEQ ID NO:1 can be eliminated. This provides for about 15 nucleic acid bases flanking the mRNA start codon. In keeping with a preferred minimum length of about 20 nucleic acid bases of an antisense polynucleotide whose sequences flank that start codon, about 8 of the 5'-terminal and 3'-terminal bases of the polynucleotide of SEQ ID NO:1 can be eliminated. This provides for about 10 nucleic acid bases flanking the start codon.

A polynucleotide containing about 50 nucleic acid bases that hybridizes to about 25 bases on either side of the TAC sequence is shown below as SEQ ID NO:7.
G G G C G A G C T G T C C A G C C G A G G G G A C-
CATTTTACGGGCGGGCGGGCAGCAGGCT (SEQ ID NO:7)
A contemplated polynucleotide has the above sequence or a shorter sequence that includes about 30 bases and hybridizes with about 15 bases flanking the mRNA start codon. A contemplated sequence can also contain substitutions for about 3 to about 5 of the bases so long as hybridization occurs with the corresponding DNA or RNA sequence under conditions of high stringency.

A further preferred polynucleotide links the terminal 1 to about 5 bases, and preferably 3 bases, of SEQ ID NO:1 by pseudophosphate bonds that are resistant to cleavage by exonuclease enzymes. Exonuclease enzymes hydrolyze the terminal phosphodiester bonds of a nucleic acid. Endonuclease enzymes hydrolyze internal phosphodiester bonds of nucleic acids.

By replacing those terminal phosphodiester bonds or even all of the phosphodiester bonds in a contemplated polynucleotide with pseudophosphate bonds that are resistant to the action of exonucleases and/or endonucleases, the stability of the nucleic acid in the presence of exonucleases and endonucleases is increased. As used herein, pseudophosphate bonds include, but are not limited to, methylphosphonate, phosphomorpholidate, phosphorothioate, phosphorodithioate and phosphoroselenoate bonds. Additionally, exonuclease-and/or endonuclease-resistant polynucleotides can be obtained by blocking the 3'- and/or 5'-terminal nucleotides with substituent groups such as acridine, caps such as 5-methylguanosine or poly(A) tails, as are well known in the art. See, e.g., Cohen (ed.), *Oligodeoxynucleotides*, CRC Press, Boca Raton, Fla. (1989); Gait (ed.), *Oligonucleotide Synthesis: A Practical Approach*, IRL Press, Oxford, England (1984).

Preferred pseudophosphate bonds are phosphorothioate bonds. A preferred polynucleotide with phosphorothioate bonds is:

N N N T C C A G C C G A G G G G A C C A T T T-TACGGGCGGGCGGNNN (SEQ ID NO:2), wherein the N's represent bases modified by phosphorothioate. The polynucleotide of SEQ ID NO:2 is sometimes referred to as MR-1.

An antisense TGF-α polynucleotide defined before in regard to SEQ ID NO:1 and 7 that has bases added or deleted as described and that also includes pseudophosphate bonds at the 5' and 3'-termini is also contemplated. Such contemplated polynucleotides are not illustrated here as their sequences are the same as those described before, with the addition of the pseudophosphate bonds such as the phosphorothioate bonds described. Base substitutions as before are also contemplated along with the before-discussed hybridization stringency requirement.

An invert polynucleotide is also contemplated. An invert polynucleotide has the order of its bases inverted so that the 5'-terminal base becomes the 3'-terminal base, the second base from the 5'-terminus is the second base from the 3'-terminus and so on. The invert polynucleotide of SEQ ID NO:1 is shown below as SEQ ID NO:8, whereas that of SEQ ID NO:7 is shown below as SEQ ID NO:9:

A C G G G C G G G C G G G C A T T T T A C C A G G G-GAGCCGACCTGTC (SEQ ID NO:8).

T C G G A C G A C G G G C G G G C G G G C A T T T T A C-CAGGGGAGCCGACCTGTCGAGCGGG (SEQ ID NO:9).

An invert polynucleotide has the same length characteristics and includes the same number of bases flanking (on either side of) the start codon as a previously defined polynucleotide. An invert polynucleotide can also include the bases that can be added to SEQ ID NO:1, except that those bases added to the 5'-terminus of SEQ ID NO:1 are added to the 3'-terminus of SEQ ID NO:8, and the sequence of the added bases is inverted. Similarly, an invert sequence can include at the 5'-terminus the bases shown previously that could be added to 3'-terminus of SEQ ID NO:1, with the sequence inverted.

A contemplated invert polynucleotide need not hybridize as discussed before, and can contain 3 to 5 substitutions to remain at least 90 percent homologous (identical) to a depicted sequence. Hybridization for an invert polynucleotide is assayed using a polynucleotide have the non-inverted sequence.

A contemplated invert polynucleotide can also include pseudophosphate bonds such as phosphorothioate bonds. A preferred human TGF-α invert polynucleotide with a phosphorothioate bonds is:

N N N G G C G G G C G G G C A T T T T A C C A G G G-GAGCCGACCTNNN (SEQ ID NO:10), wherein the N's represent bases modified by phosphorothioate bonds.

Again, as was the case previously for the previously discussed polynucleotides, an invert polynucleotide having terminal pseudophosphate bonds can contain about 20 to about 50, preferably about 30 to about 40, and more preferably about 40, nucleic acid bases with about 10 to about 25, preferably about 15 to about 20, and most preferably about 20, bases flanking the mRNA start codon. Thus, the requirements for an invert polynucleotide containing pseudophosphate bonds are the same as those for an invert polynucleotide.

The present invention is further directed to a polynucleotide of about 20 to about 50, more preferably about 30 to about 40, and most preferably about 40, nucleic acid bases in length, which polynucleotide hybridizes to the about 10 to about 25, more preferably 15 to about 20, and most preferably about 20, nucleic acid bases flanking the start codon of the mRNA encoding the receptor for human epidermal growth factor (rEGF). A preferred polynucleotide is a human rEGF antisense molecule having the sequence shown in SEQ ID NO:3.

G G C C G T C C C G G A G G G T C G C A T C G C T-GCTCCCCGAAGAGC (SEQ ID NO:3)

The polynucleotide of SEQ ID NO:3 contains 39 nucleic acid bases. That sequence includes 18 bases complementary to the 5'-side of the start codon (AUG) and can conveniently include one up to about seven further complementary further bases from the sequence of rEGF. Owing to the antisense nature of SEQ ID NO:3, additional bases complementary to the 5' flanking region of the rEGF start codon are added to the 3' end of SEQ ID NO:3, as discussed above for SEQ ID NO:1. The additions to the 3' end, from one to seven additional bases, are shown below:

T
TC
TCG
TCGC
TCGCT
TCGCTC
TCGCTCC

SEQ ID NO:3 also contains 18 bases complementary to the 3' side of the mRNA start codon. A contemplated sequence can therefore include one up to about seven additional bases of an rEGF sequence linked to the 5' terminus of SEQ ID NO:3, as shown above, again because of the antisense nature of SEQ ID NO:3. The addition to the 5' end, from one to seven additional bases, are shown below:

C
CC
CCC
CCCC
GCCCC
TGCCCC
CTGCCCC

In keeping with a preferred minimal length of about 30 nucleic acid bases of an antisense polynucleotide whose sequence flanks that mRNA start codon, and therefore includes the sequence hybridizing to the start codon near its center, three of the 5'-terminal and 3'-terminal bases of the polynucleotide of SEQ ID NO:3 can be eliminated. This provides for about 15 nucleic acid bases flanking the start codon. In keeping with a preferred minimal length of about 20 nucleic acid bases of an antisense polynucleotide whose sequence flanks that start codon, about 8 of the 5'-terminal and 3'-terminal bases of the polynucleotide of SEQ ID NO:3 can be eliminated. This provides for about 10 nucleic acid bases flanking the mRNA start codon.

A polynucleotide containing about 50 nucleic acid bases that hybridizes to about 25 bases on either side of the TAC sequence is shown below as SEQ ID NO:11.

C T G C C C C G G C C G T C C C G G A G G G T C G-CATCGCTGCTCCCCGAAGAGCTCGCTCC (SEQ ID NO:11)

A contemplated polynucleotide has the above sequence or a shorter sequence that includes about 30 bases and hybridizes with about 15 bases flanking the start codon. A contemplated sequence can also contain substitutions for about 3 to about 5 of the bases so long as hybridization occurs with the corresponding sense sequence under conditions of high stringency.

A further preferred polynucleotide links the terminal 1 to about 5 bases, and preferably 3 bases, of SEQ ID NO:3 by pseudophosphate bonds that are resistant to cleavage by exonuclease and/or endonuclease enzymes, as discussed before. Preferred pseudophosphate bonds are phosphorothioate bonds.

A preferred polynucleotide with phosphorothioate bonds is:

N N N C G T C C C G G A G G G T C G C A T C G C T-GCTCCCCGAAGNNN (SEQ ID NO:4), wherein the N's represent bases modified by phosphorothioate. The polynucleotide of SEQ ID NO:4 is sometimes referred to as MR-2.

An antisense rEGF polynucleotide defined before in regard to SEQ ID NO:3 and 11 that has bases added or deleted as described and that also includes pseudophosphate bonds at the 5' and 3'-termini as well as throughout the molecule is also contemplated. Such contemplated polynucleotides are not illustrated here as their sequences are the same as those described before, with the addition of the pseudophosphate bonds such as the phosphorothioate bonds described. Base substitutions as before are also contemplated along with the before-discussed hybridization stringency requirement.

An invert polynucleotide is also contemplated. An invert polynucleotide has the order of its bases inverted so that the 5'-terminal base becomes the 3'-terminal base, the second base from the 5'-terminus is the second base from the 3'-terminus and so on. The invert polynucleotide of SEQ ID NO:3 is shown below as SEQ ID NO:12, whereas that of SEQ ID NO:11 is shown below as SEQ ID NO:13:

C G A G A A G C C C T C G T C G C T A C G C T G G-GAGGCCCTGCCGG (SEQ ID NO:12).

C C T C G C T C G A G A A G C C C C T C G T C G C-TACGCTGGGAGGCCCTGCCGGCCCCGTC (SEQ ID NO:13).

An invert polynucleotide has the same length characteristics and includes the same number of bases flanking (on either side of) the start codon as a previously defined polynucleotide. An invert polynucleotide can also include the bases that can be added to SEQ ID NO:3, except that those bases added to the 5'-terminus of SEQ ID NO:3 are added to the 3'-terminus of SEQ ID NO:12, and the sequence of the added bases is inverted. Similarly, an invert sequence can include at the 5'-terminus the bases shown previously that could be added to 3'-terminus of SEQ ID NO:3, with the sequence inverted.

A contemplated rEGF invert polynucleotide need not hybridize as discussed before, and can contain 3 to 5 substitutions to remain at least 90 percent homologous (identical) to a depicted sequence. Hybridization for an rEGF invert polynucleotide is also assayed using a polynucleotide having the non-inverted sequence.

A contemplated invert polynucleotide can also include pseudophosphate bonds such as phosphorothioate bonds. A preferred human rEGF invert polynucleotide with a phosphorothioate bonds is:

N N N G A A G C C C T C G T C G C T A C G C T G G-GAGGCCCTGCNNN (SEQ ID NO:14), wherein the N's represent bases modified by phosphorothioate bonds.

Again, as was the case previously for the previously discussed polynucleotides, an invert polynucleotide having terminal pseudophosphate bonds can contain about 20 to about 50, more preferably about 30 to about 50, and most preferably about 40, nucleic acid bases with about 10 to about 25, preferably about 15 to about 20, and most preferably about 20, bases flanking the mRNA start codon. Thus, the requirements for an invert polynucleotide containing pseudophosphate bonds are the same as those for an invert polynucleotide.

B. The Processes

The present invention is still further directed to a chemotherapeutic process for killing or inhibiting the growth of human cancerous growth factor-sensitive cells that comprises contacting the cells to be killed or whose growth is to be inhibited in an aqueous medium under biological culture conditions suitable for growth of those cells with a chemotherapeutic amount of a polynucleotide of about 20 to about 50 nucleic acid bases in length, which polynucleotide hybridizes to the about 10 to about 25 nucleic acid bases flanking the start codon of the mRNA encoding human transforming growth factor α, the receptor for epidermal growth factor, both polynucleotides or their inverts, as described before. It is to be understood that a process can use any of the hereinbefore described polynucleotides. Contact with the polynucleotide is maintained in the aqueous medium under biological conditions for a time period sufficient for the contacted cells to be killed or their growth inhibited.

One preferred polynucleotide useful in a before-described process has the sequence shown in SEQ ID NO:1. A further preferred polynucleotide useful in a process links the terminal 1 to about 5 bases of SEQ ID NO:1 by pseudophosphate bonds that are resistant to cleavage by exonuclease enzymes. Preferred pseudophosphate bonds are phosphorothioate bonds. A preferred polynucleotide with phosphorothioate bonds is shown in SEQ ID NO:2. A still further preferred polynucleotide to the invert polynucleotide shown in SEQ ID NO:8.

In a further preferred embodiment, the chemotherapeutic process for killing or inhibiting the growth of human cancerous growth factor-sensitive cells further comprises contacting the cells with a polynucleotide of about 20 to about 50 nucleic acid bases in length, which polynucleotide hybridizes to the about 10 to about 30 nucleic acid bases flanking the start codon of the mRNA that encodes the receptor for human epidermal growth factor, both polynucleotides or their inverts, as described before. It is to be understood that a process can use any of the hereinbefore described polynucleotides.

One preferred polynucleotide useful in this process has the sequence shown in SEQ ID NO:3. A preferred polynucleotide having phosphorothioate bonds of both termini is shown in SEQ ID NO:4. A preferred invert polynucleotide having phosphorothioate bonds at both termini is shown in SEQ ID NO:14.

In a still further preferred embodiment, the chemotherapeutic process for killing or inhibiting the growth of human cancerous growth factor-sensitive cells includes the further step of contacting those cells with molecules containing an antibody combining site that immunoreacts with the receptor for human epidermal growth factor. Exemplary of such a molecule is the monoclonal autobody designated 1209-00, raised against human A431 cell membrane proteins, available from Genzyme, Inc., Boston, Mass., or MAb 425 available from Hybritech, Inc., San Diego, Calif.

The present invention is still further directed to a chemotherapeutic process for killing or inhibiting the growth of human cancerous growth factor-sensitive cells that comprises contacting the cells to be killed or whose growth is to be inhibited in an aqueous medium suitable for growth of those cells with a chemotherapeutic amount of a polynucleotide of about 20 to about 50 nucleic acid bases in length, which polynucleotide hybridizes to the about 10 to about 25 nucleic acid bases flanking the start codon of the MRNA that encodes the receptor for human epidermal growth factor. It is to be understood that this process can use any of the polynucleotides or their inverts described elsewhere herein. Contact with the polynucleotide is maintained in the aqueous medium for a time period sufficient for the contacted cells to be killed or their growth inhibited. In a preferred embodiment, the growth factor-sensitive cells are prostate cancer cells.

A preferred polynucleotide useful in this process has the sequence shown in SEQ ID NO:3. A further preferred polynucleotide links the terminal 1 to about 5 bases by pseudophosphate bonds that are resistant to cleavage by exonuclease enzymes. Preferred pseudophosphate bonds are phosphorothioate bonds. A preferred polynucleotide with phosphorothioate bonds is shown in SEQ ID NO:4. A still further preferred polynucleotide is the invert polynucleotide shown in SEQ ID NO:12.

In a further preferred embodiment, the chemotherapeutic process for killing or inhibiting the growth of cancerous growth factor-sensitive cells includes the further step of contacting said cells with a polynucleotide of about 20 to about 50 nucleic acid bases in length, said polynucleotide hybridizing to the about 10 to about 30 nucleic acid bases flanking the start codon of the MRNA for transforming growth factor α.

A most preferred chemotherapeutic process for killing or inhibiting the growth of human cancerous growth factor-sensitive cells comprises contacting the cells to be killed or whose growth is to be inhibited in an aqueous medium suitable for growth of those cells with an admixture of a chemotherapeutic amount of an above polynucleotide that hybridizes to the mRNA for human TGF-α, an above polynucleotide that hybridizes to the human rEGF, and an above molecule containing an antibody combining site that immunoreacts with the human rEGF. It is to be understood that a process can use any of the above-described polynucleotides, including inverts and as well as pseudophosphate bond-containing polynucleotides. That contact is maintained as discussed before. A process can also use any of the above-described antibodies, including that designated 1209-00 from Genzyme, and MAb 425 from Hybritech.

In a still further preferred embodiment, the chemotherapeutic process for killing or inhibiting the growth of human cancerous growth factor-sensitive cells includes the further step of contacting those cells with molecules containing an antibody combining site that immunoreacts with the receptor for human epidermal growth factor as discussed before.

As is clear from the foregoing, a process of the present invention can be practiced with one or more of the above-described polynucleotides directed against TGF-α and rEGF, including invert polynucleotides. An above process can also be practiced with any of the aforementioned polynucleotides in combination with antibodies against rEGF.

In one embodiment, the contact in an above process is carried out in vitro. In vitro contact is achieved by admixing the composition with a preparation of such cells in culture.

As used herein, a "chemotherapeutic effective amount" is that amount of a polynucleotide of the present invention that is sufficient for inhibiting the growth or killing a cell contacted with such a polynucleotide. Means for determining a chemotherapeutic effective amount in a particular subject will depend, as is well known in the art, on the nature of the polynucleotide used, the mass of the subject being treated, whether killing or growth inhibition of the cells is desired, and the like.

Actual dosage levels of active ingredients in the compositions of the present invention can be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single of divided dose may be in amounts, for example, of from about 1 nanomole to about 5 micromoles per kilogram of body weight. Dosage unit compositions can contain such amounts of such submultiples thereof as are needed to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Killing of cancerous cells can be viewed as the ultimate of growth inhibition. In vitro inhibition of growth of such cells in culture can be assayed by several well known means such as relative incorporation of a radiolabeled nucleoside such as thymidine. Suppression of prostate-specific acid phosphatase activity can also be used to measure cell growth inhibition in vitro or in vivo. In vitro cancer cell killing can also be assayed by well known techniques such as one of the several dye exclusion methods.

In vivo killing or inhibition of growth of cancer cells can be assayed by the size or tumor necrosis of the cancerous tumor such as a PC-3 tumor. On killing the cells, the tumor decreases in size and can disappear, whereas growth inhibition can be assayed against norms of growth for such tumors in humans or laboratory animals (host mammals) well known by skilled practitioners. Tumor necrosis is examined pathologically ante- or post-mortem.

In a still further preferred embodiment, the contact is carried out in vivo in a host mammal, and contact is effected by administration to the mammal of a pharmaceutical composition containing the polynucleotide dissolved or dispersed in a physiologically tolerable diluent so that a body fluid such as blood or lymph provides at least a portion of the aqueous medium. In vivo contact is maintained until the polynucleotide is eliminated from the mammal's body by a normal bodily function such as excretion in the urine or feces or enzymatic breakdown.

In a particularly preferred in vivo process discussed above, the polynucleotide is injected directly into the tumor in an aqueous medium (an aqueous composition) via a needle or other injecting means and the composition is injected throughout the tumor as compared to being injected in a bolus. For example, in the examples that follow, an aqueous composition containing antisense polynucleotide MR-1, MR-2, the inverts or mixtures thereof was injected into tumors via a needle. The needle was placed in the tumors and withdrawn while expressing the aqueous composition within the tumor. That mode of administration was carried out in three approximately orthogonal planes in the tumors.

This administration technique has the advantages of delivering the polynucleotide directly to the site of action and avoids most of the usual body mechanisms for clearing drugs. Growth factor-sensitive tumors such as prostate tumors can frequently be located by palpation so that exact placement of the polynucleotide can be carried out. In addition, modern imaging techniques such as X-ray, ultrasound and MRI can be used to locate the tumors for treatment where palpation may be insufficient to locate a tumor.

In a preferred embodiment, the growth factor-sensitive cells are prostate cancer cells. Exemplary of such cells are the before-discussed DU 145 cell line and the PC-3 cell line utilized as exemplary herein. Another growth factor-sensitive cell is the human breast adenocarcinoma cell line SK-BR-3 (ATCC HTB 30).

Biological culture conditions are conditions of temperature, pH value, osmolality, nutrient level and the like that are suitable for the growth of the cancerous cells. For in vitro usage, such conditions can be obtained from standard publications that are well known to those skilled in the art. Biological culture conditions are supplied by the animal host having the cancerous cells for in vivo usage.

The maintenance time for in vitro studies is that required to obtain the desired effects, and typically ranges from one to seven days. Maintenance times for in vivo usage are governed by normal host bodily degradation and excretion mechanisms. Because of those normal degradation and excretion mechanisms, administration of a before-discussed polynucleotide is often carried out repeatedly, particularly where systemic administration is utilized.

The present invention includes one or more polynucleotides as described above formulated into compositions together with one or more non-toxic physiologically tolerable or acceptable diluents, carriers, adjuvants or vehicles that are collectively referred to herein as diluents, for parenteral injection for oral administration in solid or liquid form, for rectal or topical administration, or the like.

A composition can be administered to mammal hosts such as humans and laboratory animals such as mice, rats, dogs and the like which laboratory animals can harbor (support the growth of) human growth factor-sensitive cancer cells, either orally, rectally, parenterally (intravenous, by intramuscularly or subcutaneously), intracisternally, intravaginally, intraperitoneally, locally (powders, ointments or drops), by diffusion from an implant or as a buccal or nasal spray. A composition is preferably administered via parenteral injection. It should also be understood that when administered in vivo, the host animal's body fluids such as blood and lymph also constitute part of the aqueous medium used to contact the cancer cells.

A composition suitable for parenteral injection can comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride and the like. Prolonged absorption of the injectable pharmaceutical form can be brought about by the use of agents delaying absorption, for example, aluminum monostearate and gelatin.

Besides such inert diluents, the composition can also include adjuvants, such as wetting agents, emulsifying and suspending agents, sweetening, flavoring and perfuming agents.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

A polynucleotide can also be administered in the form of liposomes. As is shown in the art, liposomes are generally derived from phospholipids or other lipid substances. Liposomes are formed by monoor multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are phospholipids and phosphatidyl cholines (lecithins), both natural and synthetic.

Methods of forming liposomes are known in the art. See, for example, Prescott, *Methods in Cell Biology*, Vol. XIV, Academic Press, New York, N.Y. (1976), p. 33 et seq., as well as U.S. Pat. No. 4,235,871; U.S. Pat. No. 4,501,728; and U.S. Pat. No. 4,837,838, whose disclosures are incorporated by reference.

Appropriate α, Ω-$C_4$-$C_6$ dicarboxylic acid groups can also be added at the 3' or 5' ends of a polynucleotide discussed above to join the polynucleotides to antibodies (Ab) to form chimeric molecules (chimers) for more specific delivery to the tumor, as is discussed below. Exemplary α, Ω-$C_4$-$C_6$ dicarboxylic acids include succinic, maleic, glutaric and adipic acids.

The Ab utilized immunoreacts substantially only with target tumor cells; i.e., is tumor cell specific, and thereby provides further specificity to the polynucleotides. Such an Ab-linked polynucleotide is one type of chimeric molecule of the invention.

A peptide spacer portion bonded to the polynucleotide construct can also serve to link the two portions of the molecule together. The spacer can contain zero to about 15 amino acid residues. When there are zero peptide residues present, a lysine epsilon-amino group of the Ab forms an amido bond. The spacer peptide chain, when present, is typically comprised of amino acid residues having small side chains such as glycine or alanine, or relatively hydrophilic side chains such as serine, glutamine and aspartic acid. A peptide spacer is typically free of cysteine residues, but can contain cystine residues and otherwise can have substantially any structure that does not interfere with bonding between the two portions of the chimeric compound. A peptide can be prepared by one of several synthetic methods as are well known. A particularly preferred peptide spacer includes an amino acid residue sequence that is recognized and cleaved by an enzyme such as a lysosomal or other proteolytic enzyme present within a target neoplastic cell so that the polynucleotide can be freed from the Ab after endocytosis, as is well known.

The Ab portion of the above chimeric construct can constitute an intact antibody molecule of IgG or IgM isotype, in which case, a plurality of compounds can be present per antibody molecule. The binding site portions of an antibody can also be utilized, in which case, at least one compound is linked to the proteinaceous antibody binding site portion.

An antibody binding site portion is that part of an antibody molecule that immunoreacts with an antigen, and is also sometimes referred to as a paratope. Exemplary antibody binding site portions include F(ab), F(ab'), F(ab')$_2$ and F$_v$ portions of an intact antibody molecule, and can be prepared by well known methods. An intact monoclonal antibody and a portion that includes its antibody combining site portion can be collectively referred to as a paratope-containing molecule.

Exemplary anti-tumor Ab's are the Ab against prostate specific antigen (PSA), the Ab against acid phosphatase (PAP) that are available from Hybritech, and Ab's against rEGF and TGF-α that are discussed hereinafter.

An exemplary method to illustrate that a polynucleotide could be linked to an antibody (Ab) to form a stable chimer is to first react a polynucleotide with glutaric anhydride to form the corresponding glutarate half-ester. The free carboxyl group is then converted into an N-hydroxyl succinimidyl ester. This is thereafter reacted with the Ab of choice.

The following examples further illustrate the invention and are not to be construed as limiting of the specification and claims in any way.

EXAMPLES

A. Materials and Methods

1. Antisense Compounds

Two illustrative antisense compounds of the invention were evaluated. They were synthesized to be directed towards the 18 bases on either side of the eukaryotic AUG (read ATG in cDNA) translation initiation site.

Antisense Polynucleotide Probe #1, designated MR-1 directed against the mRNA for TGF-α consisted of:
5' CTGTCCAGCCGAGGGGACCATTT-TACGGGCGGGCGGGCA 3' (SEQ ID NO:1).

A control polynucleotide was also constructed with the same nucleotide composition, however in the reverse 5' to 3' order. This is designated the MR-1 Invert:
5'ACGGGCGGGCGGGCATTTTACCAGGG-GAGCCGACCTGTC 3' (SEQ ID NO:8)

Antisense Polynucleotide Probe #2, designated MR-2 directed against the mRNA for rEGF consisted of:
5' GGCCGTCCCGGAGGGTCGCATCGCT-GCTCCCCGAAGAGC 3' (SEQ ID NO:3).

Another polynucleotide was also constructed in a similar manner and is designated the MR-2 Invert:
5' CGAGAAGCCCTCGTCGCTACGCTGG-GAGGCCCTGCCGG 3' (SEQ ID NO:12)

All of the illustrative polynucleotides were purchased from Operon, Inc., Alameda, Calif.

DNA is readily incorporated into cultured cells, apparently by an active transport mechanism [Bennett et al., *J. Exp. Med.*, 166:850–863 (1987)], which can be enhanced by temperature manipulations. Each polynucleotide, whether it be the antisense probe itself or its 5' to 3' sequence inverted control, was phosphorothioated at the 3 terminal bases at both the 5' and 3' ends to retard nuclease degradation by DNAses or RNase H. Akhtar et al., *Life Sci.*, 49:1793–1801 (1991). Antisense polynucleotides associate with lipoproteins in plasma and this affects their distribution. de Smidt et al., *Nucleic Acids Res.*, 19:4695–4700 (1991).

2. Culture of PC-3 Cells

Stock PC-3 cultures (ATCC #CRL 1435) were maintained in Ham's F12K (Irvine) media supplemented with 7 percent fetal bovine serum (Sigma), at 37° C. in a CO$_2$ incubator. For antisense studies PC-3 cells were studied in a serum free defined RPMI 1640 media supplemented with insulin (6 μg/ml), transferring (6 μg/ml), selenous acid (6 ng/ml) (collectively referred to as ITS), albumin (1.25 mg/ml) and linoleic acid (5 μg/ml). One percent solutions of penicillin and streptomycin were added throughout.

3. Stock Polynucleotide Solutions

Polynucleotides were dissolved in 0.01M Tris-HCl, pH 7.4 containing 10 mM EDTA. Before addition to cells they were diluted 1:1 with RPMI 1640/ITS/albumin/linoleic acid medium to yield the appropriate final concentration. When measured in neutral aqueous solution, 1 OD$_{260}$ nm is equivalent to 33 μg/ml of single strand DNA polynucleotide.

B. Results

1. Inhibition of PC-3 Cell Growth $8 \times 10^4$ PC-3 cells were seeded into 24 well plates in 0.25 ml of serum free RPMI 1640/ITS/albumin/linoleic acid medium in quadruplicate. Cells were permitted to adhere for two days before the addition of 10 μl of either:

(A) Oligodeoxynucleotides (12.5 μM final concentration):

(1) MR-1 (the antisense polynucleotide for TGF-α; SEQ ID NO:1);

(2) MR-2 (the antisense polynucleotide for rEGF; SEQ ID NO:3);

(3) MR-1-invert (SEQ ID NO:8);

(4) MR-2-invert (SEQ ID NO:12).

Polynucleotides were prepared by dilution in 0.01M Tris-HCl, pH 7.4 containing 1 mM EDTA. Five microliters of polynucleotide solution were added to an equal volume of complete medium (above) to yield a final concentration of 12.5 μM concentration of polynucleotides in the 0.26 ml volume.

(B) Antibodies to rEGF (1 μg/ml final concentration).

Antibody (Genzyme, #1209-00) to rEGF (anti-rEGF) was prepared in medium and consisted of 0.25 μg of anti-rEGF in a 10 μl volume, added to the 0.25 ml well volume.

Cells were cultured for 3 days before the addition of 0.26 ml of fresh medium supplemented with either polynucleotide and/or anti-rEGF antibody. Those wells that received more than one addition contained an additional 0.010 ml of medium upon each addition. Following 3 additional days of culturing, the cell number of one well was counted by hemocytometer, and the remaining cells (in triplicate) were pulsed with 2 μCi of radiolabeled thymidine. Cells were then harvested with trypsin and precipitated with 10 percent trichloroacetic acid (TCA) to determine radioactive incorporation.

Each of the polynucleotides studied inhibited thymidine incorporation, including the invert sequences (Table 1). Control cultures had a mean incorporation of 2869±272 cpm and the MR-1 and MR-2 antisense polynucleotides had incorporation of 1801±969 and 1080±20 cpm respectively.

TABLE 1

INHIBITION OF PC-3 CELL GROWTH BY ANTISENSE DEOXYPOLYNUCLEOTIDES

| Group | cpm ± SD | % Growth Inhibition | p value |
|---|---|---|---|
| Control | 2869 ± 272 | — | |
| MR-1 | 1801 ± 969 | 37% | NS |
| MR-2 | 1080 ± 20 | 62% | <0.001 |
| MR-1 + MR-2 | 502 ± 76 | 83% | <0.001 |
| MR-1 invert | 907 ± 86 | 68% | <0.001 |
| MR-2 invert | 1075 ± 347 | 63% | <0.01 |
| MR-1 invert + MR-2 invert | 759 ± 87 | 74% | <0.001 |
| anti-rEGF | 8950 ± 719 | 312% (Stimulation) | <0.001 |

TABLE 1-continued

INHIBITION OF PC-3 CELL GROWTH BY ANTISENSE DEOXYPOLYNUCLEOTIDES

| Group | cpm ± SD | % Growth Inhibition | p value |
|---|---|---|---|
| MR-1 + anti-rEGF | 667 ± 55 | 77% | <0.001 |
| MR-2 + anti-rEGF | 1696 ± 400 | 41% | <0.02 |

MR-1 is the antisense polynucleotide for TGF-α
MR-2 is the antisense polynucleotide for rEGF
MR-1 invert is the inverted 5' to 3' base sequence of MR-1
MR-2 invert is the inverted 5' to 3' base sequence of MR-2

The combination of both the MR-1 (SEQ ID NO:1) and the MR-2 (SEQ ID NO:3) polynucleotides was the most efficient with incorporation of 502±76 cpm or 83 percent inhibition (P<0.001). Each inverted control sequence was also inhibitory on PC-3 growth. The MR-1 and MR-2 inverts showed incorporation of 907±86 and 1075±347 cpm respectively, accounting for 68 percent and 63 percent respective inhibition relative to the controls and their combination accounted for 759±87 cpm and 74 percent inhibition.

These results indicate that relatively low concentrations of antisense polynucleotides directed against mRNA of TGF-α and rEGF are greatly inhibitory, especially in combination. Why inverted sequence controls are active is not known.

Suggestions have been made that invert sequence activity in other systems may be due to polynucleotide degradation that frees up unlabeled thymidine to compete with radiolabeling. This is unlikely in the present system because the MR-1 invert polynucleotide contains only 6/39 residues of thymidine, and the MR-2 invert polynucleotide contains only 5/39, yet are significantly inhibitory.

In addition, similar effects of antisense polynucleotides were observed upon cell counts. It is unlikely that these findings are the result of free thymidine competition.

Another plausible explanation is the formation of polynucleotide-directed triple helix formations. Such complexes were first described in 1957 [Felsenfeld et al., *J. Am. Chem. Soc.*, 79:2023–2024 (1957)] and recently reviewed (Durland et al., In: *Prospects for Antisense Nucleic Acid Therapy of Cancer and AIDS*, E. Wickstrom (ed), Wiley-Liss, New York, 1991, 219–226). Such complexes forming GGC and TAT triplets are possible in areas consisting of polypurine sequences, which the polynucleotides of the present invention do contain.

The effect of anti-rEGF on growth was particularly interesting, yielding 8950±719 cpm (312 percent stimulation) compared to control cultures. The combined effects of either MR-1 and MR-2 upon rEGF-induced stimulation were, however, significantly inhibitory (p<0.01; Table 2, below). MR-1 inhibited rEGF-induced stimulation 93 percent (from 8950±719 to 667±55 cpm) and MR-2 by 82 percent (from 8950±719 to 1696±400 cpm). Cell counts confirmed these findings.

TABLE 2

INHIBITION OF ANTI-rEGF INDUCED STIMULATION OF PC-3 CELL GROWTH BY ANTISENSE POLYNUCLEOTIDES

| Group | cpm SD | % Inhibition | p value |
|---|---|---|---|
| anti-rEGF | 8950 ± 719 | — | — |
| MR-1 + anti-rEGF | 667 ± 55 | 93% | <0.001 |
| MR-2 + anti-rEGF | 1696 ± 400 | 82% | <0.001 |

MR-1 is the antisense polynucleotide for TGF-α
MR-2 is the antisense polynucleotide for rEGF The stimulation produced by anti-rEGF antibodies was another unexpected finding because it demonstrated the inhibitory effects of MR-1 and MR-2 in this context. Apparently the binding of anti-rEGF antibodies alone acts as if they were ligands (EFG or TGF-α) and induces chronic stimulation, similar to the blastogenesis initiated in B lymphocytes by the addition of anti-Ig, or in the case of Grave's Disease, stimulation of the receptor for thyroid stimulating hormone by anti-thyroid antibody.

This stimulation was not found in the study by Murthy [Murthy et al., *Biochem. Biophys. Res. Commun.*, 172:471–476 (1990)], who found MAb 425 directed towards rEGF inhibited mitogenesis as well as secondary messengers stimulated for release by TGF-α exposure. It is apparent that even in the presence of extreme stimulation produced by anti-rEGF, both polynucleotides MR-1 and MR-2 were capable of great inhibition (93 percent and 82 percent respectively).

Histochemical staining studies with antibodies against TGF-α and rEGF show that PC-3 cells incubated as described with MR-1/MR-2 (for thymidine labeling) have reduced levels of TGF-α and rEGF expression. The antibody against TGF-α was obtained from Peninsula Laboratories, Belmont, Calif. (#RAS 8040); the rEGF antibody was that obtained from Genzyme.

2. Effects of LNCaP Cells

LNCaP (LNCaP•FGC, ATCC CRL 1740)cells are testosterone-dependent prostate cancer cells, and therefore differ from the autocrine-sensitive PC-3 cells in that LNCaP cells are not as sensitive to the effects on the receptor for EGF, but are sensitive to the hormone testosterone.

LNCaP cells were grown as described above for PC-3 cells, and similar studies were conducted on these cells. The results are shown in Table 3.

TABLE 3

| Treatment | cpm ± SD | LNCaP Cells % Inhibition | p value |
|---|---|---|---|
| Control | 3882 ± 2264 | — | — |
| MR-1 | 767 ± 515 | 80% | <0.05 |
| MR-2 | 1322 ± 1635 | 66% | NS |
| MR-1/MR-2 | 1221 ± 1210 | 69% | NS |
| MR-1-invert | 1432 ± 1113 | 63% | NS |
| MR-2-invert | 3641 ± 1246 | 6% | NS |
| MR-1-/MR-2-inverts | 514 ± 467 | 87% | <0.05 |
| anti-rEGF | 1772 ± 1243 | 54% | NS |
| anti-rEGF/MR-1 | 664 ± 245 | 83% | <0.05 |
| anti-rEGF/MR-2 | ND | | |

Each of the polynucleotides assayed inhibited radiolabeled thymidine incorporation, including the invert sequence controls (Table 3), and no stimulatory effect of anti-rEGF was observed. The LNCaP cells were more difficult to work with in vitro where they were hard to dissociate and tended to form more clumps than the PC-3 cells. Greater standard deviations were observed utilizing the LNCaP cells and despite the appearance of inhibition, statistical significance (p<0.05) was shown only in three groups (MR-1, MR-1/MR-2 inverts, anti-rEGF/MR-1). LNCaP cells are therefore less susceptible to manipulations directed at TGF-α and the rEGF, consistent with a better differentiated, hormone-sensitive tumor, presumably less dependent on autocrine growth factors.

3. Effects on Nude Mice In Vivo

A study utilizing two nude mice bearing the human PC-3 prostatic tumor was performed to assay the effect of the antisense polynucleotides on the serum levels of prostate-specific acid phosphatase. A single mouse was injected on two consecutive days with both the MR-1 and the MR-2 polynucleotides. Each aqueous composition was administered in the three approximately orthogonal planes of the tumor, with the aqueous composition being injected while the needle was being withdrawn from the tumor. A total volume of 0.125 ml of RPMI was injected directly into the tumor. Contained in this volume was 200 μg (15 nmol) of MR-1 and 198 μg (15.5 nmol) of MR-2. The second mouse received similar injections of RPMI alone. The following day the mice were exsanguinated, tumors were removed and fixed, and total and tartrate-resistant (prostate-specific) acid phosphatase determinations were performed by a calorimetric assay utilizing para-nitrophenyl-phosphate as the substrate.

ACID PHOSPHATASE ACTIVITY

| Mouse | Total | Non-Prostate Specific | Prostate Specific |
|---|---|---|---|
| Control | 0.448 U | 0.434 U | 0.014 |
| MR-1/MR-2 Treated | 0.393 U | 0.393 U | 0 |

1 BLB = 16.7 U/L

Histologic evaluation of paraffin embedded sections, performed by a board certified pathologist, revealed hemorrhagic necrosis with inflammatory cell infiltrates in the polynucleotide treated tumor. In addition the serum derived from the treated mouse showed 100 percent suppression of the prostate-specific acid phosphatase activity following combined treatment with the MR-1 and MR-2 polynucleotides. Histochemical staining of the frozen tumors also showed that the treated tumor had obviously reduced cytoplasmic tartrate sensitive prostate specific acid phosphatase activity.

In a similar study, MR-1 and MR-2 each at about 200 μg were separately injected into different PC-3 tumors in nude mice and a mixture of the two polynucleotides (about 200 μg of each) was injected into another tumor. Each treatment produced necrosis of the tumor cells with the mixed polynucleotides providing more necrosis than either polynucleotide alone. It is presently unknown if that greater necrosis resulted from the larger dose administered or because both antisense polynucleotides were used.

4. Rat Prostate Cancers in Rats

Similar studies were conducted on rat prostate adenocarcinomas in Copenhagen X Fischer F1 rats bearing Dunning R3327 AT-3 tumors. Although the tumors showed some necrosis, histologic evaluation suggested the necrosis to be due to cytotoxic T cell activity and was not a result of the antisense polynucleotides. These results indicate that the human antisense polynucleotides were specific for the human tumors. The results of this study also indicate that the tumor growth inhibitions observed in the nude mouse system with human autocrine-sensitive (growth factor-sensitive) prostate cancer cells were due to the polynucleotides and not an unknown impurity or toxin that may have been present in the aqueous compositions.

Although the present invention has been described in some detail by way of illustration and example for purposes of clarity and understanding, certain obvious modifications can be practiced within the scope of the appended claims.

I claim:

1. A polynucleotide of about 20 to about 50 nucleic acid bases in length, said polynucleotide hybridizing under conditions of high stringency to the about 10 to about 25 nucleic acid bases flanking the start codon of the mRNA for human transforming growth factor α that is an antisense molecule consisting of the sequence shown in SEQ ID NO:1.

2. A polynucleotide of about 20 to about 50 nucleic acid bases in length, said polynucleotide hybridizing under conditions of high stringency to the about 10 to about 25 nucleic acid bases flanking the start codon of the mRNA for human transforming growth factor α wherein the terminal 1 to about 5 bases are linked by pseudophosphate bonds that are resistant to cleavage by exonuclease or endonuclease enzymes and consisting of the sequence shown in SEQ ID NO:2.

* * * * *